(12) United States Patent
Mian et al.

(10) Patent No.: US 9,389,205 B2
(45) Date of Patent: *Jul. 12, 2016

(54) RESONANT SIGNAL ANALYSIS-BASED INSPECTION OF RAIL COMPONENTS

(71) Applicant: International Electronic Machines Corporation, Troy, NY (US)

(72) Inventors: Zahid F. Mian, Loudonville, NY (US); William B. Johnson, Mechanicville, NY (US)

(73) Assignee: International Electronic Machines Corp., Troy, NY (US)

( * ) Notice: Subject to any disclaimer, the term of this patent is extended or adjusted under 35 U.S.C. 154(b) by 214 days.

This patent is subject to a terminal disclaimer.

(21) Appl. No.: 13/900,764

(22) Filed: May 23, 2013

(65) Prior Publication Data

US 2013/0312524 A1 Nov. 28, 2013

Related U.S. Application Data

(60) Provisional application No. 61/688,842, filed on May 23, 2012.

(51) Int. Cl.
*G01N 29/12* (2006.01)
*G01N 29/44* (2006.01)

(52) U.S. Cl.
CPC ............ *G01N 29/12* (2013.01); *G01N 29/4427* (2013.01); *G01N 2291/2696* (2013.01)

(58) Field of Classification Search
CPC ................... G01N 29/12; G01N 2291/2696
USPC .................................. 73/579, 593, 659, 660
See application file for complete search history.

(56) References Cited

U.S. PATENT DOCUMENTS

| 4,402,210 A | 9/1983 | Vandeberg |
| 4,487,071 A * | 12/1984 | Pagano ................. G01N 29/07 73/612 |
| 4,976,148 A | 12/1990 | Migliori et al. |

(Continued)

FOREIGN PATENT DOCUMENTS

| JP | 2000203419 | * | 7/2000 |
| JP | 2000203419 A | | 7/2000 |

(Continued)

OTHER PUBLICATIONS

Ahn Jae Yul, International Search Report and Written Opinion for PCT/US2013/042361, Sep. 2, 2013.

(Continued)

*Primary Examiner* — J M Saint Surin
(74) *Attorney, Agent, or Firm* — LaBatt, LLC

(57) ABSTRACT

A solution for evaluating the condition of a rail component based on resonant response profiles across a set of bands of vibrations. The vibrations can be induced into the target component during normal operation of the target component. The resonant response profile of the rail component can vary depending on wear or damage, and thus can be used to determine whether the rail component can safely remain in use. An embodiment comprises an isolated segment of rail of a length selected to allow a single railroad wheel on it at a time, with a set of devices which can induce specific vibrations into the wheel as it passes, and another set of devices which can acquire the resonance signals from the wheel.

21 Claims, 11 Drawing Sheets

(56) References Cited

U.S. PATENT DOCUMENTS

| | | | |
|---|---|---|---|
| 5,062,296 A | 11/1991 | Migliori | |
| 5,351,543 A | 10/1994 | Migliori et al. | |
| 5,355,731 A | 10/1994 | Dixon et al. | |
| 5,408,880 A | 4/1995 | Rhodes et al. | |
| 5,425,272 A | 6/1995 | Rhodes et al. | |
| 5,571,966 A | 11/1996 | Tsuboi | |
| 5,636,026 A | 6/1997 | Mian et al. | |
| 5,680,054 A * | 10/1997 | Gauthier | B61L 23/044 246/121 |
| 5,837,896 A | 11/1998 | Rhodes et al. | |
| 5,952,576 A | 9/1999 | Schwarz | |
| 5,992,234 A | 11/1999 | Rhodes et al. | |
| 6,523,411 B1 | 2/2003 | Mian et al. | |
| 6,768,551 B2 | 7/2004 | Mian et al. | |
| 7,213,789 B1 | 5/2007 | Matzan | |
| 7,640,139 B2 | 12/2009 | Sahara et al. | |
| 7,693,673 B2 * | 4/2010 | Luo | B61K 9/04 246/169 A |
| 8,112,237 B2 | 2/2012 | Bartonek | |
| 8,140,250 B2 | 3/2012 | Mian et al. | |
| 8,326,582 B2 | 12/2012 | Mian et al. | |
| 8,577,546 B2 | 11/2013 | Gunther et al. | |
| 2009/0188320 A1 | 7/2009 | Greenough et al. | |
| 2010/0161255 A1 * | 6/2010 | Mian | G01N 29/041 702/56 |

FOREIGN PATENT DOCUMENTS

| | | | |
|---|---|---|---|
| JP | 2003213602 | * | 7/2003 |
| JP | 2004-085273 | | 3/2004 |
| KR | 10-2011-0047743 | | 5/2011 |

OTHER PUBLICATIONS

Saint Surin, Jacques M., U.S. Appl. No. 14/074,986, Non-Final Office Action, Apr. 2, 2015, 16 pages.

Mutkins, Karyn, Australian Examination Report, Application No. 2013266261, Jun. 22, 2015, 4 pages.

Saint Surin, Jacques M., U.S. Appl. No. 14/074,986, Notice of Allowance, Nov. 20, 2015, 30 pages.

Chinese Application No. 201380026533.0, Office Action with machine Translation to English, Apr. 26, 2016, 23 pages.

* cited by examiner

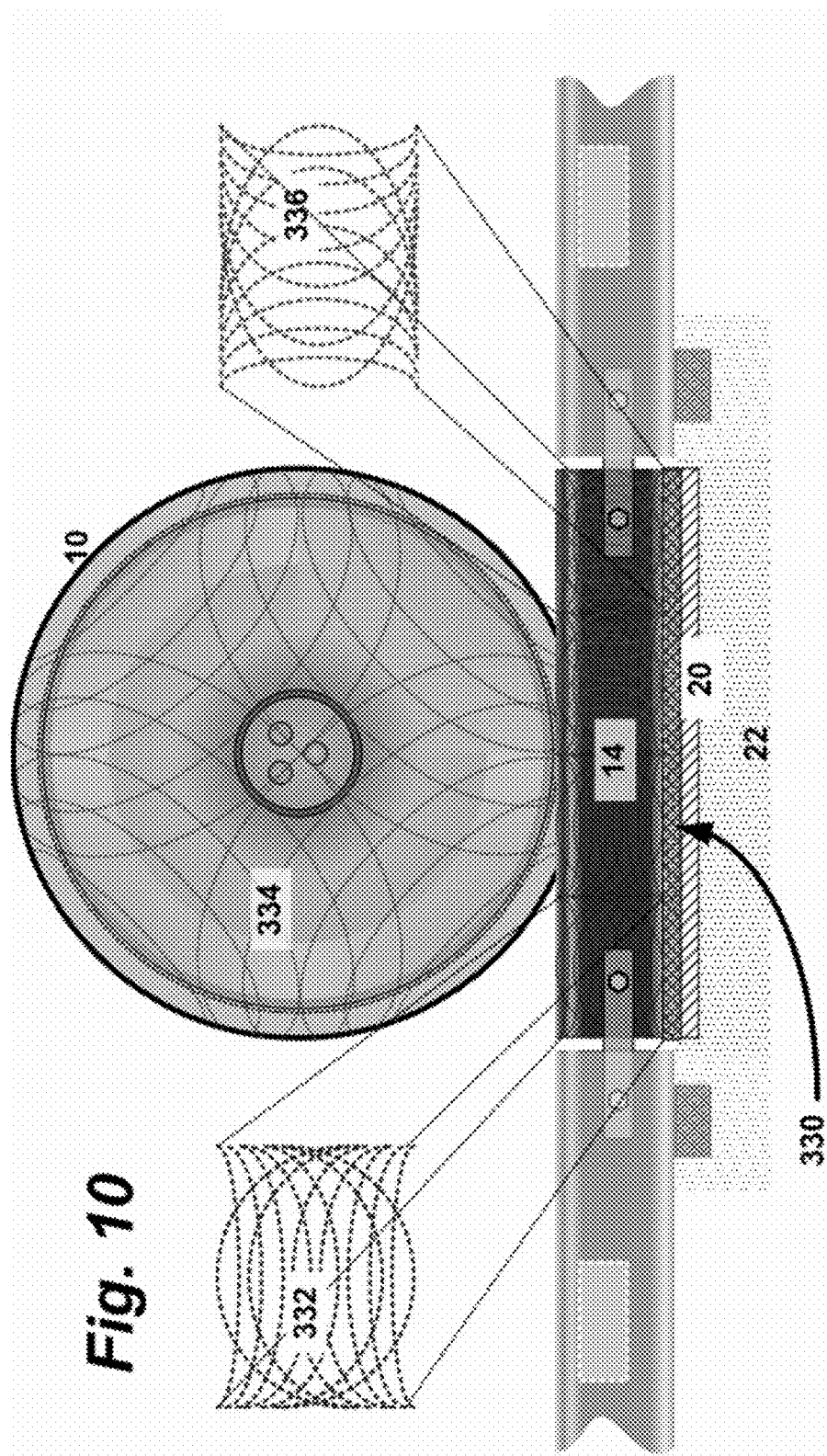

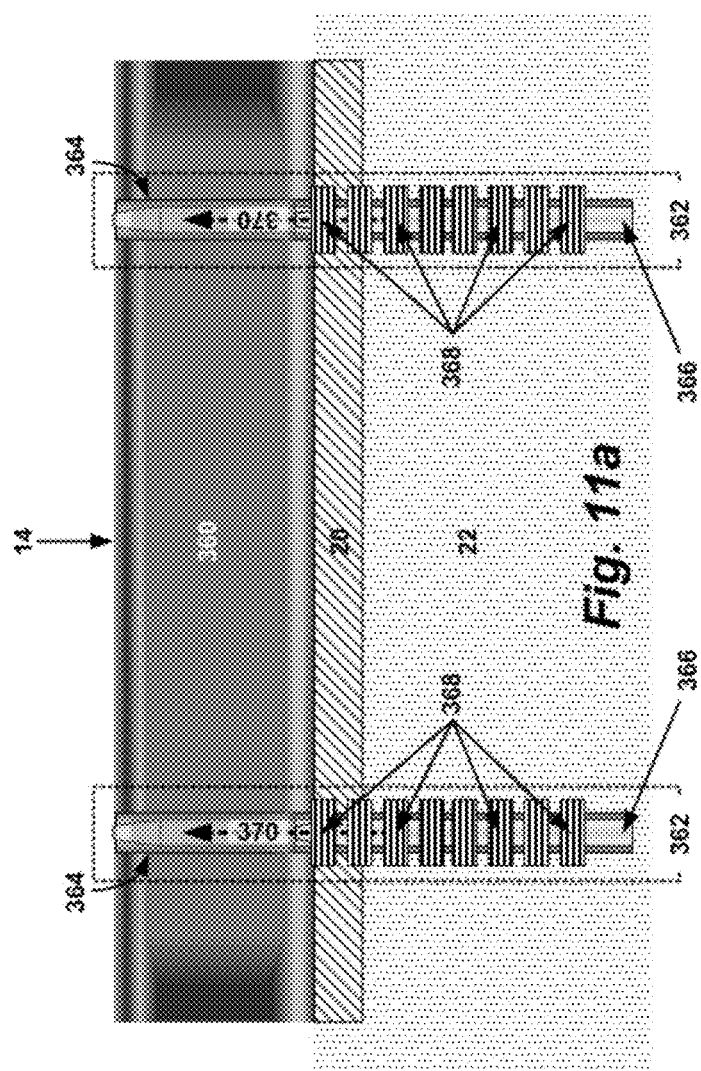

RESONANT SIGNAL ANALYSIS-BASED INSPECTION OF RAIL COMPONENTS

REFERENCE TO PRIOR APPLICATIONS

The current application claims the benefit of U.S. Provisional Application No. 61/688,842, titled "Ultrasonic analysis-based inspection system and method for rail components", which was filed on 23 May 2012, and which is hereby incorporated by reference.

TECHNICAL FIELD

The disclosure relates generally to nondestructive inspection of vehicle components, and specifically to a new and innovative solution for evaluating a condition of railroad wheels and/or other components of a rail transportation system.

BACKGROUND ART

Evaluation of the resonance of an object to various acoustic input frequencies has been known as a method for determining the condition of metallic or otherwise highly rigid objects or components for centuries. In fact, some uses of this principle may pre-date the industrial revolution. With respect to rail, early British railroad engineers would tap the wheels of a train and use the sound to determine if a crack was present. Of course, bell makers rely on resonances for their products to work at all. In one approach, a simple physical striker (similar to a ball-peen hammer under automatic control) and comparison of the resulting acoustic spectra of wheels on both sides of an axle is used to determine if one wheel is bad, under the assumptions that (A) the spectra of two good wheels should be very similar, and (B) that it is very unlikely for two wheels on one axle to have defects so similar as to produce nearly-identical spectra. Note that this second assumption may not be entirely valid. For example, slid-flats are caused by the locking of a brake and the subsequent friction between wheel and rail causing flat wear in one location on the wheel. In this case, one would expect the flat area of wheels on the same axle to be very nearly identical. In another proposal, a preliminary acoustic-signature inspection system using a similar hammer-based approach was designed and tested, but only achieved 45% identification of known flawed wheels with a false alarm rate of almost one third.

Other methods of using sound to determine the presence of a defect in such objects are known. For example, the inventors previously proposed electromagnetically inducing acoustic signals into a wheel (electromagnetic acoustic transduction) and tracking the nature and timing of the returned signals. However, this method, and related ultrasonic inspection methods, are specifically focused on locating and identifying very specific flaws.

Resonant frequencies are dependent on the material characteristics of an object. In general, this relationship may be described as follows:

$$f_r \sim \sqrt{\frac{k}{m}},$$

where $f_r$ is a resonant frequency of the object, k is a measurement of the "stiffness" of the object (Young's Modulus), and m is a general symbol for mass which may take into account the dimensions and density of the object. As a complex object is made up of material which may have multiple boundaries and even differing compositions and stresses therewithin, it is in effect made up of many different sub-objects, and just as a combination of a violin body and string resonate in a specific way, the sub-objects themselves as well as the various combinations of these sub-objects may have resonances. Thus, there may be many thousands of resonances in any given object. In theory, as all components of a heterogeneous solid have their own resonances, and the interaction of these components will introduce resonances and resonance shifts directly related to the size, shape, and composition of those components, it is possible to completely describe the entire object—crystalline structure, inclusions, shape, size, material composition—in terms of its resonances.

While this ultimate application of resonances may be forever relegated to theory due to physical and computational constraints, the important point is that any significant wear on a component will change its dimensions (and thus m and resonant frequencies), and a defect (such as a crack) in a component will change the stiffness of the component in that location, leading to an overall change in k and thus also in one or more of the relevant resonant frequencies. Conversely, for objects manufactured to adequate tolerances which are in good condition, all resonances would be expected to be very close together. This means that a "resonance spectrum"—a scan across all the emission frequencies of the vibrating object which shows all of the significant resonant peaks—for any "good" component should be very similar, and any flawed component will noticeably depart from that spectrum, regardless of what the exact nature of the defect may be. This differs significantly from the previously described approach comparing wheels on opposing sides of an axle as a specific spectrum or spectra are known for "good" components and there is no reliance on assumptions of goodness. Moreover, the previously described approach of comparing wheels on opposing sides of an axle does not focus on resonances, which are specific characteristics of the spectrum, focusing instead on the general correspondence of the spectra overall.

Numerous patents and commercial applications are found for this basic approach, which is generally called resonant ultrasound spectroscopy (RUS). A group of related approaches teach the use of this method to determine when manufactured components fall outside of some set of specifications. These teach various additions and extensions of the principle, such as using the method to determine sphericity of a given component, temperature compensation for resonant spectra, prediction of resonant frequencies of specific components to allow limiting of the scanned bandwidth in diagnostic testing, and using shifts between "wet" and "dry" spectra to determine the presence or absence of cracks or crack-like flaws in a component. Together, these approaches have resulted in several commercial applications for testing of manufactured components and for determination of characteristics of materials, such as those offered by Magnaflux' Quasar systems and Mechtronic's Vibrant NDT.

All of the above approaches apply to components of a known shape (with some variation depending on dimensional specifications, etc.) placed in a testing location, and isolated from all other components. To date, none of these approaches have been used in field settings, in general because most mounted components have connections/attachments to other components which can suppress, damp, or unpredictably change the expected resonances. The other generally related methods, faced a number of additional difficulties in that they had a bandwidth-limited approach, did not isolate the rail segment, could not use current signal-processing techniques, and so on. Current uses of RUS are for isolated and relatively small components, generally either undergoing post-manufacture inspection or being examined for suspected flaws, or for materials characterization. In both cases, the sample or component is placed in a very specialized holder and isolated. Large components have historically presented issues with the amount of energy needed to properly evoke the resonances.

SUMMARY OF THE INVENTION

The invention described herein is intended to overcome one or more of the limitations of current art methods of detecting various faults or flaws in rolling stock components for railroad applications. More specifically, embodiments of the invention allow the determination of whether a rail component, such as a wheel, is at risk of failure in the future. The basic concept involves the use of the resonance of a wheel to various acoustic input frequencies. Aspects of the invention can include one or more of the following innovations:

Use of RUS and related methods on in-situ (operating) components in a complex machine (e.g., wheels mounted and rolling on a railcar or locomotive) and use of RUS on large components.

Use of multiple "pingers" or of adjustable piezoelectric/electromagnetic pingers to cover multiple frequencies.

Use of a parabolic dish rather than a standard microphone to permit longer sample capture at greater standoff and superior signal-to-noise ratio.

Use of a sound-based parametric model using invariant feature sets which represent a particular wheel or a type of wheel, and which can be modified for wheel wear, size, etc.

Use of trending analyses on a captive fleet of wheels (e.g., in a transit setting) in conjunction with the above parametric model approach to directly track the condition of specific wheels throughout their lifetime. Trending can permit prediction of the expected changes in resonance for that specific wheel, and make any departures from that expectation much more easily noticed than, for example, a parametric model based only on a single idealized wheel or set of "average" wheels at a given state of wear.

Use of established databases (e.g., UMLER) to recognize wheel type, manufacturer, etc., in freight settings, allowing the parametric model to be adjusted in "real-time" to fit each wheel being measured.

Use of an isolated segment of rail to eliminate interference of vibrations from other wheels on rail.

Use of an isolated segment of rail as an actual input transducer for the resonance-inducing signal.

Other innovations are also described herein.

In an embodiment, the invention comprises some device or devices for inducing resonances in the target object (in an embodiment, a railroad wheel), the same or other device or devices for recording the resonances induced across some set of frequencies, and some means of analyzing and comparing these resonances.

An embodiment induces resonances in a moving railroad wheel for the purpose of comparing the resonant signals returned by the wheel with either a known representative signal for a railroad wheel of that type, or prior resonant signals from the same wheel, to determine whether a defect exists or has developed which makes the wheel unsafe to use. This provides a "go-no go" decision-making system which is most useful to railroad operation.

A first aspect of the invention comprises a device for inducing resonances into a railroad wheel or potentially other targets and then receiving the resonance signals from the target object, even while said object is moving and an operating component of a larger system such as a railcar.

A second aspect of the invention comprises a system for inducing, acquiring, and analyzing resonance signals from target objects and determining the overall condition of the objects in a "field" setting.

A third aspect of the invention comprises a method for determining an overall condition of railroad wheels and similar target objects by use of the device and system described herein.

The illustrative aspects of the invention are designed to solve one or more of the problems herein described and/or one or more other problems not discussed.

BRIEF DESCRIPTION OF THE DRAWINGS

These and other features of this invention will be more readily understood from the following detailed description of the various aspects of the invention taken in conjunction with the accompanying drawings in which:

FIG. 1a shows a side view of the device, FIG. 1b shows a front view of the device, while FIG. 1c shows a diagram of the device as a component of the system.

FIG. 10 is a diagram of an embodiment of the invention in which the rail itself comprises the interrogation portion of the system.

FIGS. 11a and 11b show a diagram of an embodiment illustrating a through-rail method of exciting a railroad wheel.

DETAILED DESCRIPTION OF THE INVENTION

Figure 1:
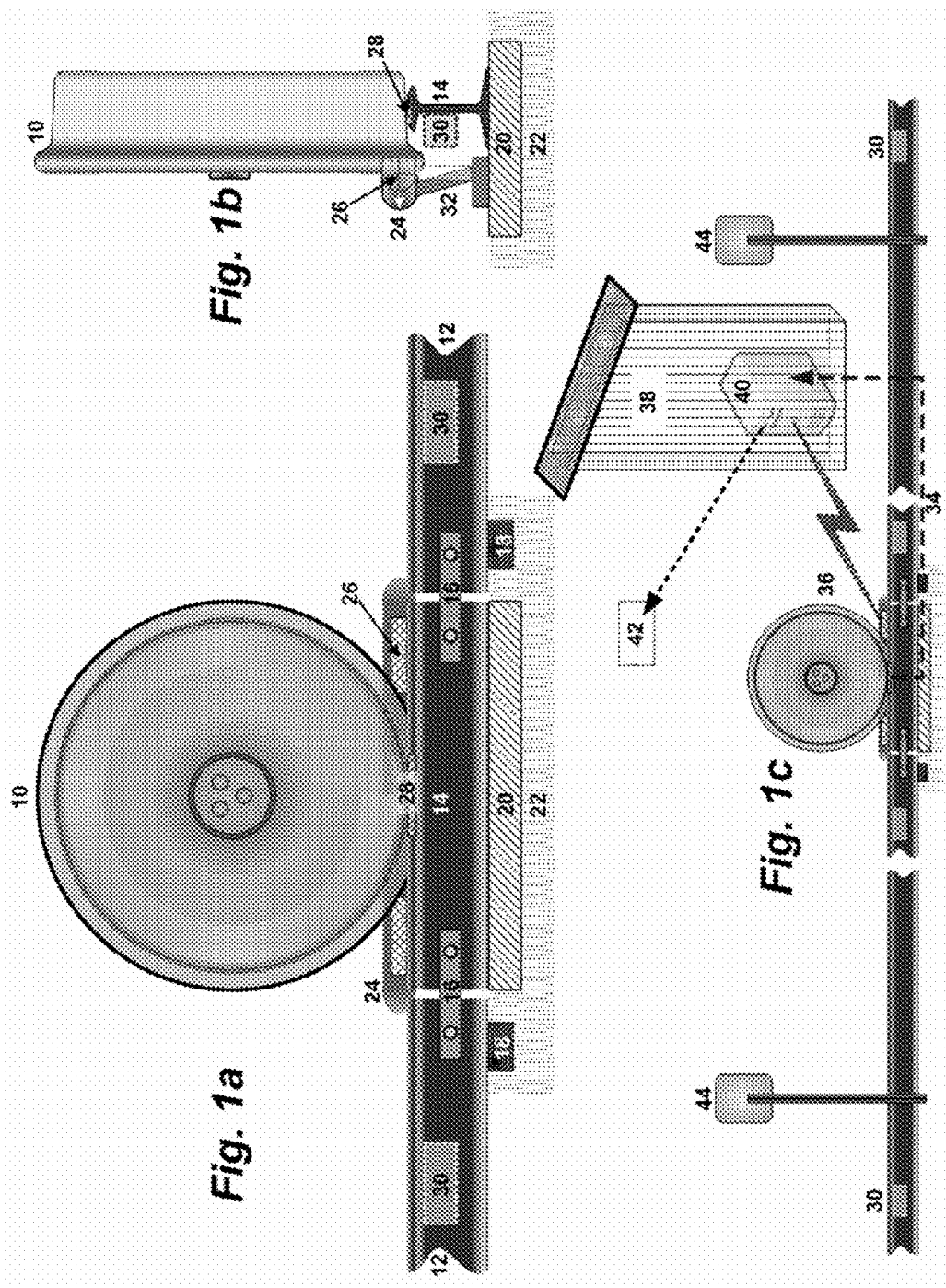
FIGS. 1a-1c show views of an illustrative device and system according to an embodiment.

FIGS. 1a-1c depict views of an illustrative device and system according to an embodiment with two variations. As seen in FIG. 1a, railroad wheel 10 is traveling down a set of rails 12, and travels over an isolated rail segment 14. Isolated segment 14 is connected to the remaining rails 12 by connecting devices 16 which prevent the rail segment 14 from moving with respect to rails 12 without strongly coupling the segment 14 and the rails 12. An illustrative connecting device 16 comprises joint bars (sometimes referred to as "fishplates"), which can be made from a glass-reinforced epoxy laminate, such as G-10, or a similar composite having high strength and internal damping. The connecting device 16 isolates rail segment 14 from the vibrations caused by other wheels 10 in front of and behind the current wheel 10. Furthermore, while rails 12 are supported by standard ties 18, the rail segment 14 can be mounted on a vibration absorbing or isolating structure 20, e.g., embedded in standard fill 22. An illustrative isolating structure 20 can comprise an isolating substrate, elastomers (e.g., as in Pandrol's "Vanguard" system), and/or the like. As the wheel 10 travels along the isolated segment 14, it contacts either of two different means for inducing and receiving resonances. A sensor head 24 is designed and mounted in such a manner that the sensor head 24 maintains contact with the wheel 10 during its passage, allowing transducers 26 located on the sensor head 24 to induce and receive vibrations from the wheel 10. Furthermore, a transducer 28 may be mounted directly into the rail head of the isolated rail segment 14 itself. These transducers 26, 28 may be piezoelectric, electromagnetic, physical impact, or any other means of inducing vibration at some known frequency or frequencies into the wheel 10. The transducers 26, 28 may also themselves function as the receivers of the acoustic vibrations from the wheel 10, or there may be separate receiver devices. An illustrative embodiment uses piezoelectric transducers to both induce and receive signals, but other embodiments can use other means.

In an embodiment, the rail segment 14 may be composed of different materials than the rails 12. A different material may be selected for one or more of a number of reasons, including but not limited to, improved noise damping capabilities (to minimize environmental noise input), improved ability to permit maintenance/replacement of other components, ease of modification and repair, or (as described herein) so as to serve in some manner as a more active component of the system.

The system can include wheel detectors 30 mounted to the rail 12 at some distance from the isolated rail segment 14. These detectors 30 can serve one or more purposes, including for example, to "wake up" the system when a new train enters the system after some time has passed; to ready the system to take readings of each wheel 10 as it passes, by noting the speed of the wheel and giving a good estimate of time-of-arrival; and/or the like. Individual wheel detectors exist which incorporate both the detection function and the speed-measurement function. FIG. 1*a* shows two detectors 30, one on each side of the isolated rail segment 14. In an embodiment of the system, two or more detectors 30 can be located on each side of the isolated rail segment 14 and be separated by some distance less than the circumference of a train wheel, thus permitting measurement of the forward speed of the wheel 10 through the interval between the first and second detectors 30 detecting the passing wheel 10.

The system is shown including detectors 30 on each side because in many cases the rail 12, 14 may be used in both directions. The exact distances from the isolated rail segment 14 that the wheel detector(s) 30 are to be placed will be variable depending on the precise design and setting of the system. It is understood that the same detectors 30 may not be used for the train detection/wakeup function as for the wheel time-of-arrival estimate. In an embodiment, approaching train detectors can be located considerably farther from the isolated rail segment 14 in order to provide sufficient advance notice to ready the system and thus permit a much greater level of shutdown of the electronic components of the system between trains.

The front view of the system shown in FIG. 1*b* illustrates one possible embodiment of the side-mounted sensor head 24. In this case, each end is flared/bent in such a way as to cause sensor head 24 to be pushed away from the rail segment 14 on a flexible or spring mount 32, while still being held inward firmly to maintain good contact with the wheel 10. It is understood that the exact amount of movement permitted/necessary can be variable and the distance shown in FIG. 1*b* should not be taken as prescriptive. Nor should the precise design for the side-mounted sensor head 24 be taken as the only way in which such a sensor head can be designed.

In any event, FIG. 1*c* shows that the data or signals resulting from the operation of the sensor head 24 and/or the embedded transducer head 28 on the wheel 10 are sent either via wired 34 and/or wireless 36 data link(s) to a computer system 40. One or more components (e.g., computing devices) of the computer system 40 can be located, for example, in a local data processing shed, within which is a set of computing devices with appropriate processing software and hardware to perform at least a portion of the data acquisition and/or analysis on the data described herein. The data and/or results of processing may be stored locally or may be sent to a remote location 42, at which one or more additional components of the computer system 40 are located. In an embodiment, some or all data processing can be performed by and/or additional data can be acquired from a computer system, distinct from the computer system 40, located at the remote location 42.

In addition, FIG. 1*c* shows more-distant wheel detectors 30 as discussed herein, for use in initial wheel detection and system wakeup functions, and further shows car identity sensors 44 which may use radio frequency identification (RFID) signals from applied RFID tags as are often used in freight settings, more active radio sensing, data from a routing/scheduling central control system as may exist in a transit setting or some other method to ascertain the identity of the passing car. Inclusion of the car identity sensors 44 can provide an ability to match specific wheels 10 to specific cars and axles, which can be useful for a variety of purposes, especially for predictive maintenance, as discussed herein.

As implied by the discussion of resonances, there are potentially many thousands of resonances across the full usable spectrum of vibrations inducible in railroad wheels 10 (e.g., from 1-10 Hertz (Hz) up through hundreds of megahertz (MHz)). Searching for all such resonances across the full spectrum is a highly computationally intensive task, requires significant time to sweep across all frequencies, produces very large amounts of data for analysis, and can require generally more expensive and complex equipment to sweep across such a large band. In an embodiment, the system focuses on a set of narrow bands in which there will be found resonances which will convey only the truly necessary information as to whether the wheel 10 is structurally sound to an extent that it may continue to be used without danger.

At the same time, an embodiment of the system can provide multiple resonance peaks for comparison. In this case, normal process and wear variations can produce changes in a number of resonance peaks. If used in isolation, the variation in these peaks due to manufacture and wear variations may be great enough to mask the variation caused by relatively small but potentially significant flaws. By taking multiple resonances as an overall spectrum or pattern, the variation in all selected resonances can be shown to be a useful and reliable indicator of wheel condition despite small individual variations. In an embodiment, the system utilizes multiple resonances of interest, which occur across a wide range of frequencies.

One solution to determine these specific bands of interest is to take a large number of wheels, both flawed and unflawed, and subject them to intensive resonant analysis, examining all resonance peaks for correlation with various states. For improved accuracy, one could perform this analysis on various classes/categories of wheels, distinguished by size, specific wheel profile, composition, wear dimensions, and other qualities/characteristics. This is, however, an extremely labor and time-intensive task.

In an embodiment, a model of the resonance of a railroad wheel is used to determine a set of general bands of interest. Unlike many other modern transportation devices and components, the railroad wheel remains virtually unchanged from those manufactured fifty or a hundred years ago, and is in essence a relatively simple object of a reasonably homogeneous material which lends itself well to modeling. It has been demonstrated that a railroad wheel can be reasonably modeled as a small set of rings elastically coupled to each other. This provides a mechanism for determining specific general bands of interest for this application, which can be further defined by real-world testing, especially for determining general shifts or changes in the ultrasonic spectrum caused by regular wear conditions rather than by flaws of a dangerous nature.

In addition, the railroad wheel is sufficiently robust that a great deal of energy can be imparted to it as part of an interrogation without causing significant harm. This permits the use of ultrasonic spectroscopy on such a large component. Prior art approaches have not attempted to use this approach on very large components because of the difficulty of imparting a sufficient excitation to the component to provide enough signal to be able to reliably obtain a good spectrum of the component. Most components are not constructed nearly as ruggedly as railroad wheels, nor easily able to be placed in a setting where very high power interrogation pulses can be administered. A rail yard provides an illustrative setting where extremely forceful impact events (e.g., rail car coupling) are a routine matter and thus adding a few such events are of no consequence in this setting.

In order to induce resonances, the transducer 26, 28 can be capable of producing vibrations at the specified bands. In an embodiment, the system includes piezoelectric transducers, as such transducers have been created which have a very wide potential spectrum of vibration. However, it is understood that use of piezoelectric transducers is not a requirement or limiting condition. For example, depending on the exact bands of interest, the conditions of the test, and other factors, other methods may be used, including EMAT, physical impact, or others.

The basic process of inducing resonance can include the transducer 26, 28 producing some frequency of vibration for a period long enough to induce a resonance, if such is present, and after an appropriate interval, switching to another frequency to be examined. This is called "sweeping" the spectrum. In an embodiment, a sweep of all bands of interest takes time on the close order of 100 milliseconds, or about $1/10^{th}$ of a second. Any person familiar with the art of such "sweeping" can recognize how this time period may be affected by the characteristics of the resonance delay, the specific frequency "step" interval to be used, and/or other characteristics involved with the generation of such signals and sampling of return signals in this manner.

The system further includes a receiver for the acoustic data generated by these vibrations. In an embodiment, the receiver is an integral part of the transducer 26, 28. For example, the receiver may be separate piezoelectric components or be part of an extended piezoelectric array, but will be embodied as a part of the entire transducer component. However, it is understood that other embodiments may use microphones (depending on the frequency bands of interest), electromagnetic means of detecting vibration (EMAT, etc.), laser vibrometer, or any other method of sensing sound/vibration in the bands of interest.

The receiver for the resonance data can be either identical with, or closely co-located with and similar or identical in operating principle to, the transducer 26, 28. A required sweep duration can be used to determine a lower bound for an overall size of the transducer contact area based on a target speed of the rail wheels 10. In an embodiment, the system is located in a classification yard (e.g., hump yard) or other train yard, at some point in the yard where, if a flawed wheel 10 is identified, the rail vehicle may be routed to a repair facility, e.g., to have the wheel set replaced. Low travel speeds are required in such locations. Assuming a speed no higher than five miles per hour (mph), the contact area should be approximately nine inches (approximately 8.8 inches in a more particular embodiment) in length. Some additional length may be desired to provide some margin for error and potential for redundancy to be introduced into the data for noise reduction and other processing. A maximum possible size for the transducers (and thus providing a theoretical maximum speed at which the system may be used) can be determined by the minimum distance between wheels (otherwise a new wheel will have entered the sensing area of the system before the first has exited). This will vary depending, for example, on whether the system is applied to a freight or transit application, as transit vehicles have different wheel spacing than freight trains, in general. For a wheel spacing of approximately 2.4 meters, seen in transit applications, the maximum speed works out to slightly over fifty mph.

Figure 2:
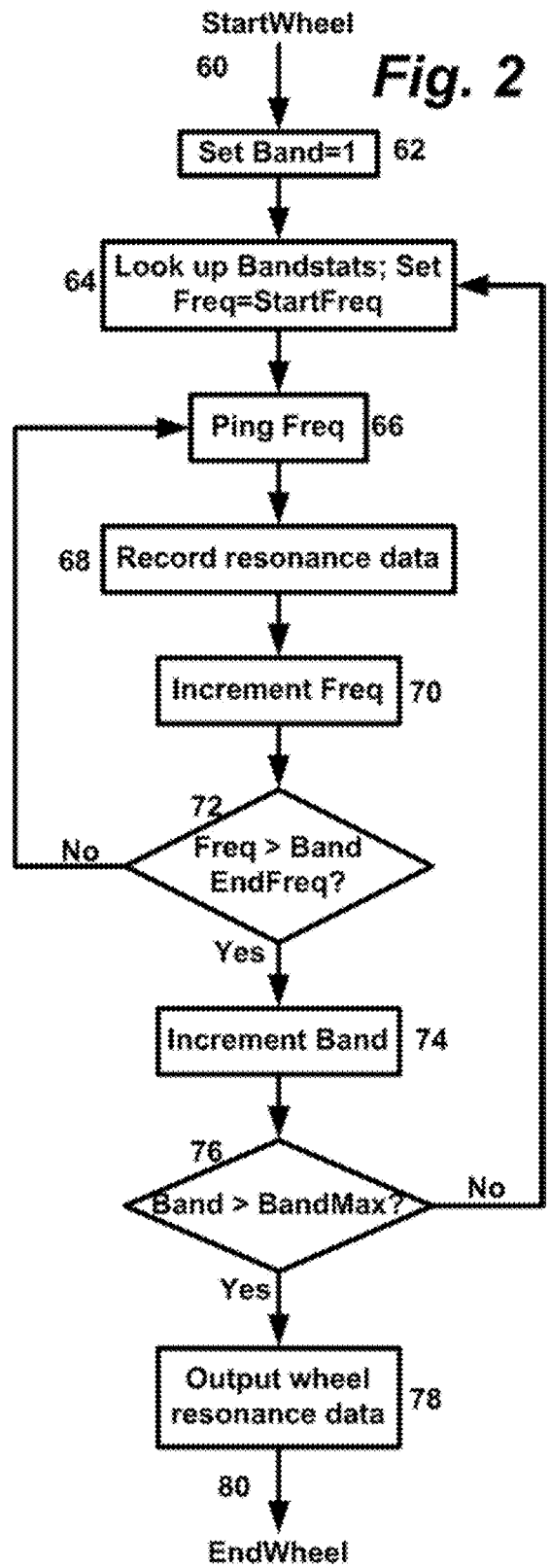
FIG. 2 shows a flowchart diagram of an illustrative process for imparting and gathering resonance data according to an embodiment.

FIG. 2 shows a flowchart of an illustrative process for performing a sweep of some number of frequency bands for resonances according to an embodiment. The computer system 40 (FIG. 1c) can store a reference table of the frequency limits of each band, and the signal transducer 26, 28 (FIG. 1a) can be capable of generating all the required frequencies. At action 60, the computer system 40 begins collecting data with a new wheel 10. In action 62, the computer system 40 can set the band to the first sweep band. In action 64, the computer system 40 can look up the statistics (e.g., start frequency, sweep interval/increment, end frequency, and/or the like) for the corresponding band and set the start frequency accordingly. In action 66, the computer system 40 can operate the transducer 26, 28 to ping the wheel 10 at the set frequency, and in action 68, record any induced resonances. In action 70, the computer system 40 can increment the frequency and in action 72, perform a check to determine if the increment places the frequency past the limits of the band. If the frequency is still in-band, the process returns to action 66, in order to ping the new frequency. Otherwise, in action 74, the band is incremented, and in action 76, the new band designation is checked to determine if the number of bands has been exceeded. If not, the process returns to action 64 to look up band statistics and set the start frequency. If the number of bands has been exceeded, in action 78, the collected resonance data can be processed, passed on to a main computing device for processing (e.g., located at a remote location 42 (FIG. 1c)), and/or the like, and in action 80, the evaluation and the sweep of the wheel 10 is finished.

Figure 3:
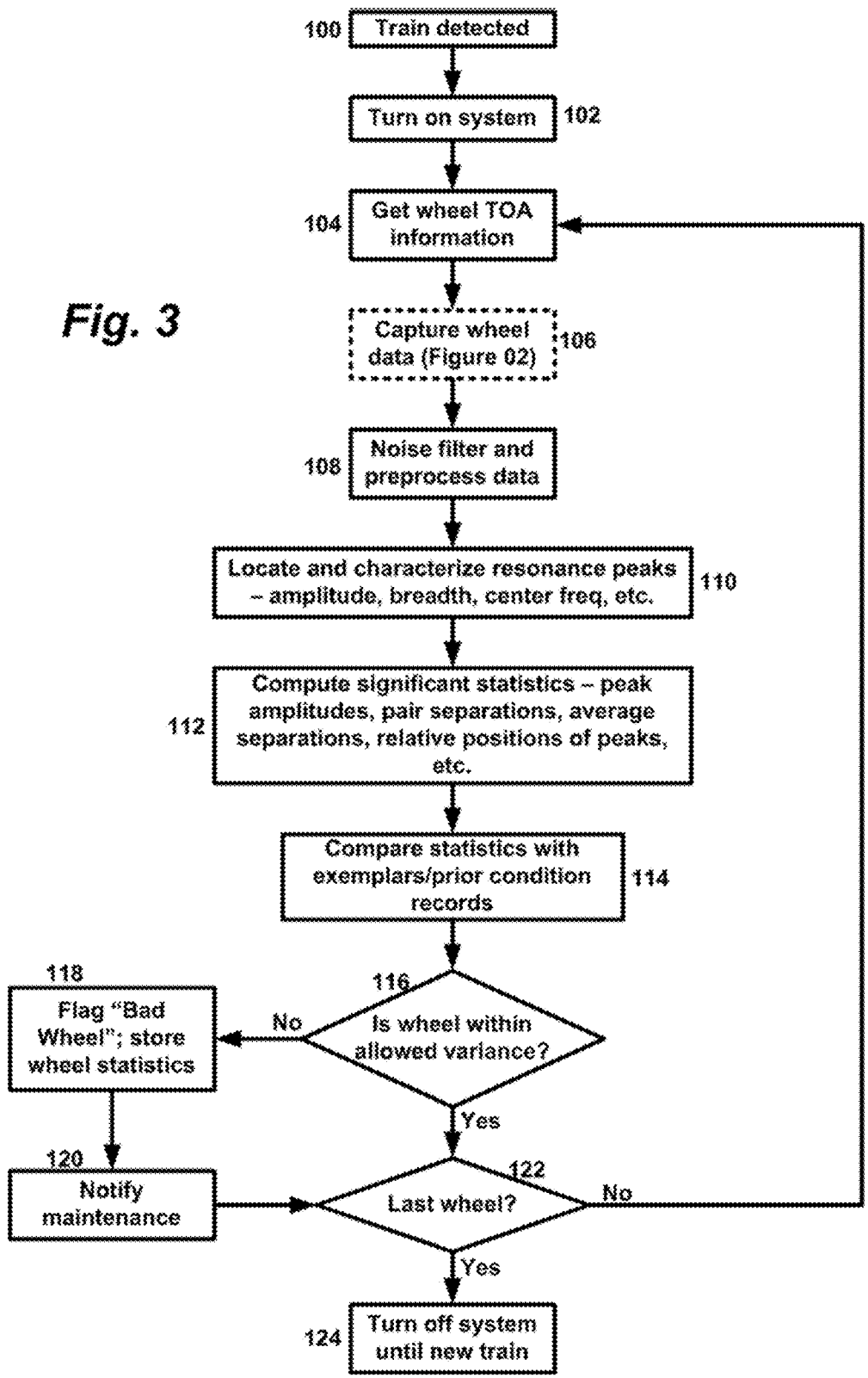
FIG. 3 shows a flowchart diagram of an illustrative process for the system according to an embodiment.

This process is, however, only one part of the overall system functionality. FIG. 3 shows a flowchart diagram of an illustrative process of the overall operation of the system according to an embodiment. Initially, the system can be in a state of dormancy, e.g., possibly completely shut down, with the exception of a subsystem which is watching for approaching rail vehicles. In action 100, a rail vehicle (e.g., as part of a train) is detected 100. In action 102, the system is awakened. In action 104, a wheel time-of-arrival (TOA) is determined and can be used to properly time the acquisition of data in action 106, e.g., using a process as previously detailed in FIG.

2. If the rail vehicle and/or wheel 10 identity is known (through, for example, a previously illustrated vehicle identity sensor subsystems 44), this data can be associated with (e.g., attached to) the wheel resonance data acquired during that cycle. In action 108, the acquired data may be subjected to additional noise filters and/or other preprocessing to bring out the features of the signals of interest and suppress others which may obscure the signal or interfere with the analysis thereof. Some examples of these preprocessing/noise filter approaches include high-cut, low-cut, and band pass filters, normalization, ambient noise cancellation through a running-average or more complex means of characterizing background noise/vibrations, and/or the like.

In any event, in action 110, the computer system 40 can subject the preprocessed data to analysis to locate and characterize the resonance peaks present in each band of data. Some illustrative characteristics of interest in the data can include (but are not limited to) the amplitude (peak height above "normal") of each resonance, breadth (width) of the peak above a certain cutoff, the center frequency of each peak, shape of the signal overall (symmetrical/asymmetrical, etc.), and/or others. Once these characteristics have been determined by the computer system 40, in action 112, the computer system 40 can compute a number of key statistics/emergent signal features or metrics. These statistics may include, but are not limited to, the number of peaks seen in each band, separation of specific peak pairs, average separations of various peaks, relative position of peaks, and/or the like.

Following the computation of the statistics/metrics of interest, in action 114, the computer system 40 can compare these metrics with either modeled expectations, statistics of various exemplar wheels (for example, a series of similar wheels in varying conditions), with prior data from that specific wheel, if known, and/or the like. In an embodiment, the system is installed in a setting, which involves a "captive fleet" of locomotives and passenger cars which will routinely pass a given point on a known schedule. In a more particular embodiment, the setting is a transit setting, as such predictable movement of vehicles is not generally true of a freight setting, in which the ownership and routing of a given car may change drastically over a period of a year, to the point that a car originally in CSX territory and controlled by CSX in, say, April, may be in Union-Pacific territory and controlled by Union Pacific in June, and in the hands of a third party by August, and not return to CSX territory for months or even years after that. Being part of a "captive fleet" with regular return visits to the location of the system permits the system to compile regular records of changes in the ultrasonic spectral profile of each wheel 10 and, from these records, be able to predict with much greater accuracy, expected changes in that profile due to wear and any trends indicative of potential failure.

In any event, whatever method of comparison is used, in action 116, the computer system 40 decides whether the wheel 10 is within allowed variance. If the variance is outside of permitted parameters, in action 118, the computer system 40 can flag the wheel 10 as bad and the data can be associated with the flag. In action 120, the computer system 40 can notify maintenance, e.g., by wired or wireless means, as required by the employing railroad or facility. In an embodiment, the computer system 40 can activate an automated routing system, which can shunt the rail vehicle directly to a repair track, while in other embodiments, the computer system 40 can notify the operating individuals or organization of the need for maintenance. Following action 120 or following after a determination in action 116 that the wheel 10 is within allowable bounds, in action 122, the computer system checks to verify as to whether this is the last wheel 10 to be processed (e.g., last wheel in a train). If not, the process returns to action 104 to begin the acquisition and testing of the next wheel 10. If it is the last wheel 10, in action 124, the system can be shut down until another set of rail vehicles arrives.

The analysis of the resonance spectrum may proceed on a number of parameters which may be determined from the spectrum. These parameters can include, but are not limited to, the number of resonance peaks seen within a given band, the height or amplitude of the peaks, the specific frequency around which a given resonance peak is centered, the distances between a set or sets of resonance peaks, and/or the like. FIGS. 4a-4d illustrate some of these possible changes.

Figure 4:
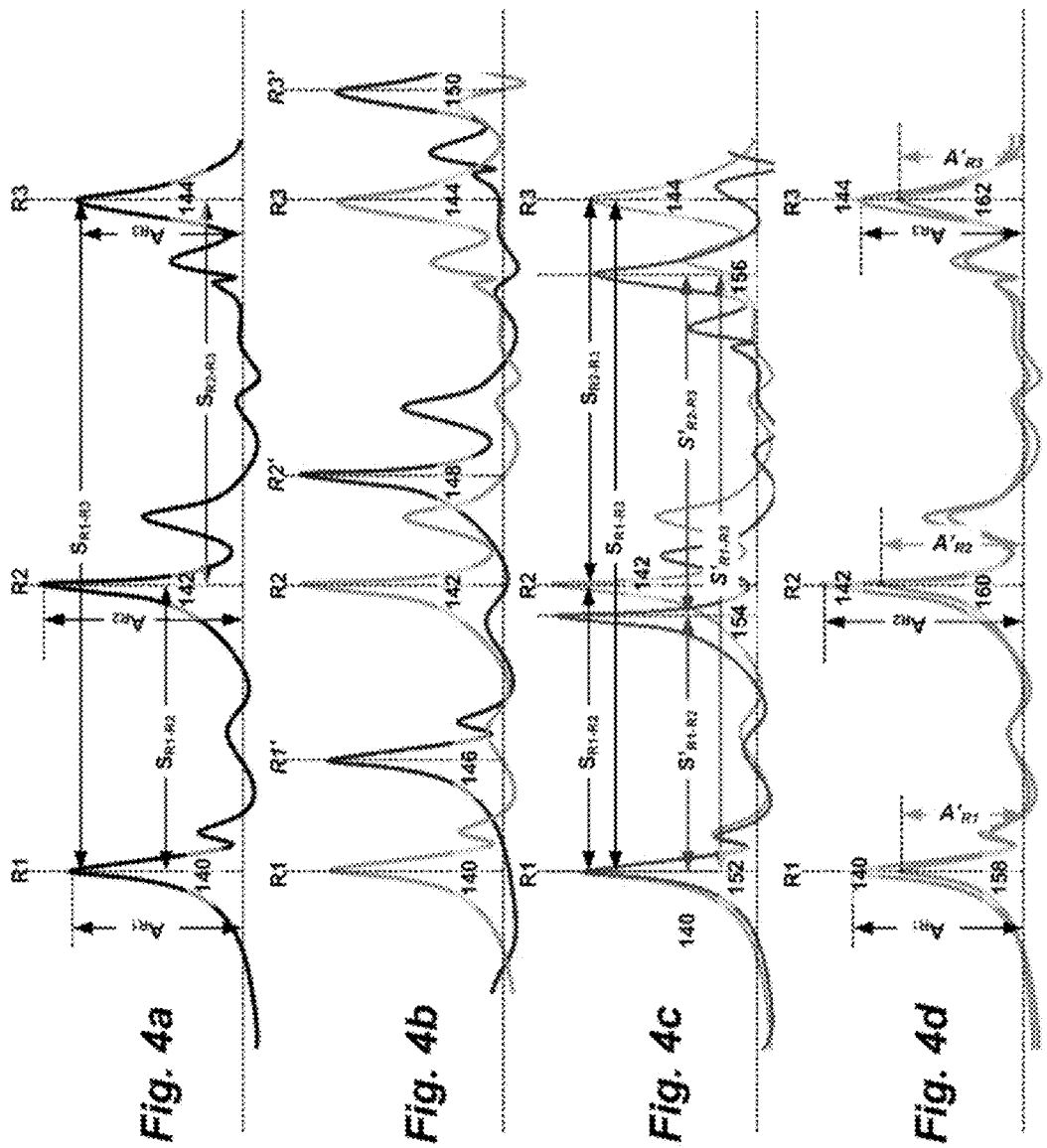
FIGS. 4a-4d show several examples of how resonance signatures may change from their ideals according to an embodiment.

FIG. 4a shows a selected set of three resonance peaks, specifically resonance peak 140, resonance peak 142, and resonance peak 144. Note that these are conceptual diagrams and are not intended to represent any particular set of resonances that may or may not be present in any particular object at any particular set of frequencies. Each resonant peak 140, 142, 144 has a central resonant frequency Rx, where X denotes some number or symbol specifying an individual peak. For resonance peak 140 X=1, for resonance peak 142 X=2, and for resonance peak 144 X=3. Similarly, each resonant peak 140, 142, 144 has a height or amplitude, $A_{RX}$, and there exists for each pair of resonance peaks an inter-peak separation $S_{Rx-Ry}$, where X and Y denote the specific peaks involved in the separation, which is measured between the central resonant frequencies $R_X$ and $R_Y$. For example, resonance peak 142 has central resonant frequency R2, amplitude of $A_{R2}$, and its separation from resonance peak 144 is $S_{R2-R3}$. These are all illustrated in FIG. 4a.

In any event, any or all of these characteristics may vary. FIGS. 4b-4d illustrate variance in these parameters. FIG. 4b demonstrates a resonance shift in which the amplitudes $A_{RX}$ and inter-peak separations $S_{Rx-Ry}$ remain constant, but the location of the resonant peaks RX shifts. Instead of the original peaks 140, 142 and 144, the spectrum shows shifted peaks 146, 148, and 150, whose central resonant frequencies instead of being R1, R2, and R3 are, respectively, now R1', R2', and R3'.

FIG. 4c illustrates a condition in which the positions of the resonant peaks have changed with respect to each other, causing inter-peak distances to change. Instead of original peaks 140, 142, and 144 there are shifted peaks 152, 154, and 156. Note that peak 152 is essentially identical to peak 140 and with an essentially identical central resonant frequency R1, but peak 154 and 156 are progressively farther from their respective equivalents 142 and 144. Because of this, there is a clear difference in the inter-peak separations. Most obviously, one can compare $S_{R1-R3}$ between peaks 140 and 144 with $S'_{R1-R3}$.

FIG. 4d shows a condition in which the amplitudes of the resonant peaks have changed. Instead of original peaks 140, 142, and 144 there are damped or diminished peaks 158, 160, and 162, so that instead of (for example) peak 140's amplitude of $A_{R1}$, we now see the corresponding peak 158's amplitude of $A'_{R1}$.

Any of these characteristics may be used to signify a change in the target object, and the degree of difference which is considered significant may be determined for each object separately or be determined more generally from theoretical or experimental data. These examples are simple and illustrative and should not be considered to be either exhaustive or exclusive illustrations of methods and/or parameters for determining the "fit" of a given spectrum to an exemplar spectrum of a theoretical or ideal component or prior spectrum of the identical component during an earlier measurement. In embodiments, any or all of these approaches may be used separately or in combination (for instance, one might look for a change in amplitude combined with a shift in center frequencies), or in different ways than illustrated or in combination with other parameters not yet illustrated. For example, patterns of change across multiple peaks could be compared. A shift in amplitude of resonance peak 142 with no corresponding shift in amplitude of 140 or 144 might be accorded a different significance than a general lowering of the amplitude. For example, the former might represent a crack or weakening of a particular portion of the structure, while the latter could simply be a degraded signal due to excessive dirt/shelling/etc. on the wheel 10. No method or combination of methods for analyzing the resonant spectra of the target components is explicitly or implicitly excluded from use in embodiments described herein.

In any event, these characteristics, combinations of these characteristics, and others may be used to construct a parametric model of good wheels or other components based on the features (specific parameter conditions and relationships) seen in the acoustic/ultrasonic spectral bands selected. A similar approach is described in U.S. Pat. No. 8,326,582, which is herein incorporated by reference. In the patent, specific faults or flaws of railroad wheel bearings are detected and identified through the comparison of various features as exemplified by the presence, intensity, and/or absence of specific sorts of signal characteristics in specified bands. The determination/identification of these features may involve a number of different types of analysis on the basic signal characteristics, including (but not limited to) amplitude of specific peaks, inter-peak separations, minima and maxima across each selected band, averages across some number of points of data, variance across the sample, RMS, kurtosis, etc.

With these and other features/characteristics determined, the computer system 40 can determine, from those features/characteristics, whether the target component is good or bad. Theoretical modeling and/or experimental data may be used to assign thresholds of "good" or "bad" to each of the selected features, and across the entire set of features the computer system 40 can perform analyses to determine which features are most significant and reliable in indicating the condition of the component. In an embodiment, the computer system 40 can use multiple independent parameters, which have been shown to result (in work associated with the referenced patent and in other work) in a highly reliable classification system, which accurately discriminates between acceptable and unacceptable components. In an embodiment, the computer system 40 confirms or denies that the wheel remains usable for some considerable period of time. In this case, the specific flaw does not matter, all that matters is whether the wheel 10 must be replaced.

As described herein, the system can be used on a rail system, such as a transit rail system, in which there is a "captive fleet" of vehicles—a set of vehicles which stay within the system and routinely traverse known locations at reasonably regular intervals. This permits the system to inspect the same vehicle's components in a generally known schedule, and by so doing accumulate data on the changes which occur in the resonance spectra of the target components as a consequence of normal use.

Figure 5:
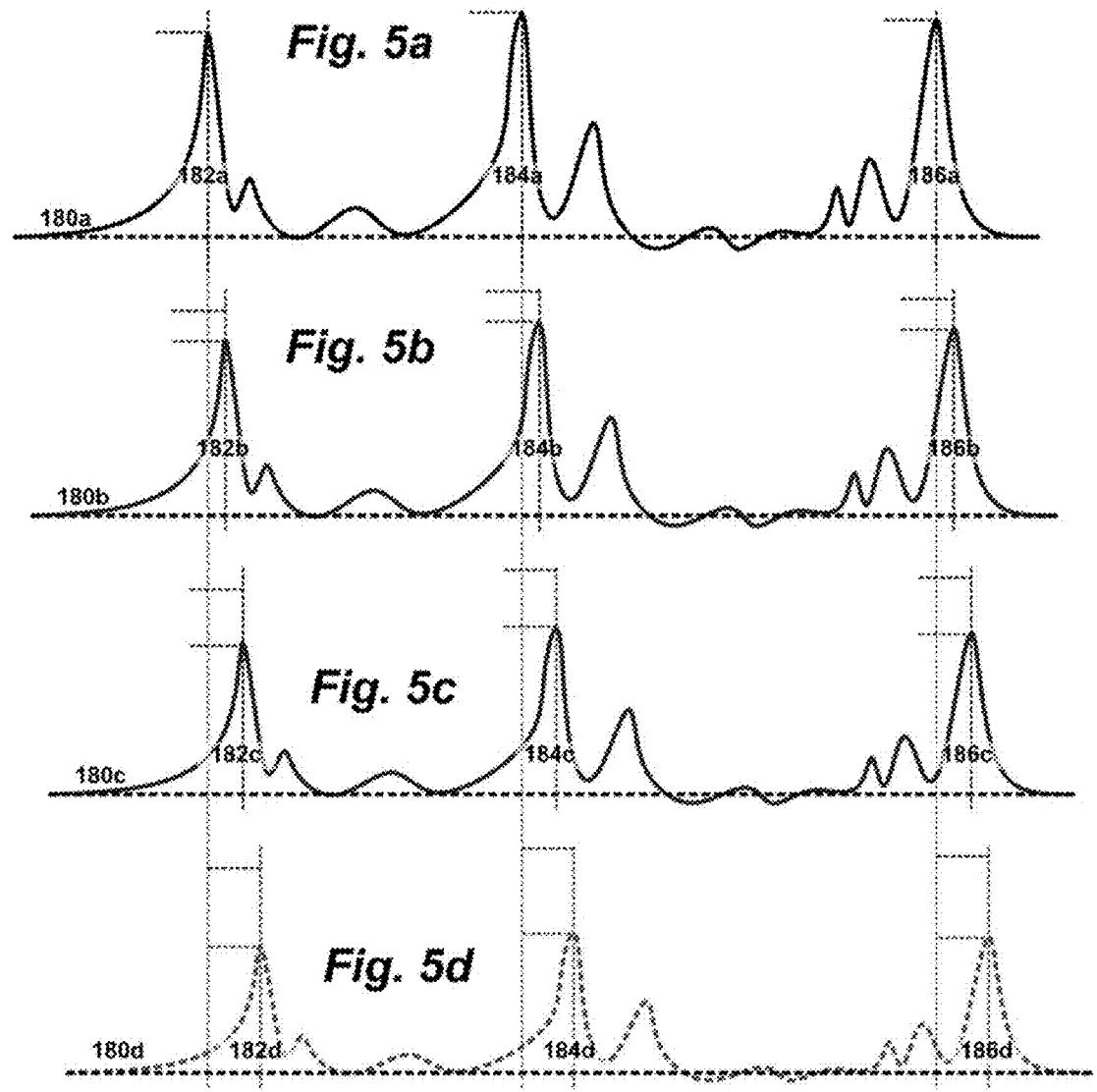
FIGS. 5a-5d show a conceptual diagram of the possible effects of long-term wear on a resonance signal according to an embodiment.

FIGS. 5a-5d show an exemplary illustration of this principle. It is understood that an actual version can be much more detailed and complex. In FIG. 5a, an example section 180 of a resonance spectrograph of a particular wheel as it first passes through the system is shown, with three resonance peaks 182a, 184a, and 186a. Each of the resonance peaks has an amplitude and central resonant frequency indicated. In FIGS. 5b and 5c, the same section of the spectrum of the same wheel on two successive later passes through the system are shown. As can be seen, in each of FIGS. 5b and 5c, the amplitude of spectrographs 180b and 180c successively decreases, and the central frequency shifts upward (to the right). From this, knowing the interval that has passed between the acquisition of 180a and 180b, and between 180b and 180c, the computer system 40 can determine a trend of the change of the spectrograph, and predict what the next reading should look like. In this case, the main peaks should have decreased in amplitude by roughly the same amount and shifted up the spectrum similarly. This predicted graph 180d is shown in FIG. 5d, with peaks 182d, 184d, and 186d.

This permits the computer system 40 to have increased diagnostic accuracy and reliability due to an ability to account for specific wear and use related changes which are not related to safety-related flaws. Additionally, the computer system 40 can determine trends in the data of individual components and predict: (A) what the expected spectrum should be after some interval; and (B) when certain types of wear-related failure are likely to occur, and thus for how many more use cycles the component should be permitted to operate.

Figure 6:
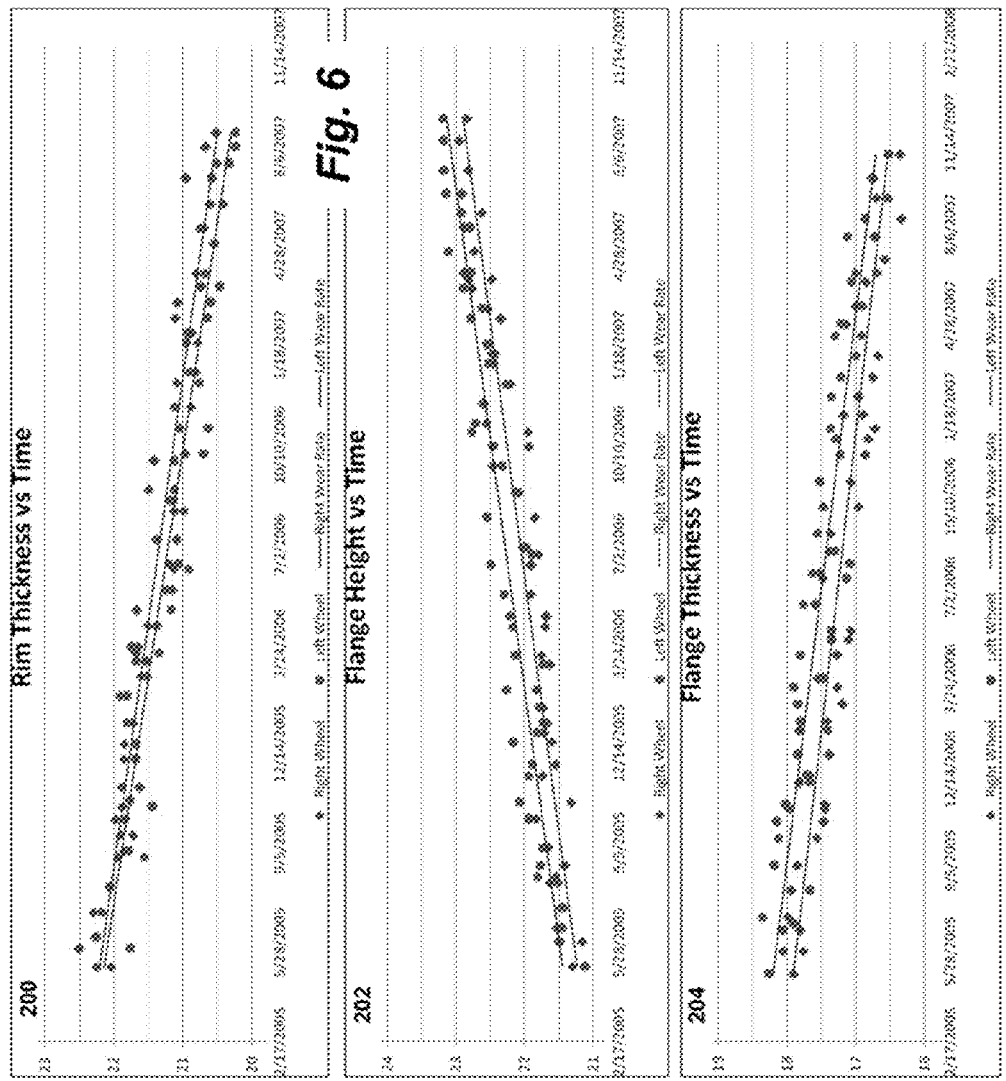
FIG. 6 shows a set of trends in actual wheel parameters over time.

As a result, the computer system 40 can perform predictive health maintenance (PHM) of the target components. It is understood that the example described herein is only illustrative, and is merely intended to illustrate the principle behind the approach. In application, such trends are likely to be more complex, depending on physical wear effects on the target component. For example, FIG. 6 shows three graphs of wear trends on actual freight train wheels according to an embodiment. The first graph 200 shows the wear trend of rim thickness over time, the second 202 shows the change in flange height over time, and the third 204 shows the wear effect on flange thickness over time. The interaction of these different dimension changes on various resonances could be extremely complex, resulting in very nonlinear graphs which would require considerable processing to model and project accurately. Nonetheless, the same basic principles apply, and can provide a huge advantage for the safety and economical maintenance of a "captive fleet" setting.

Either a local computing device or computing devices located at a remote location 42 can perform the processing described herein. In addition, an embodiment of the computer system 40 can improve upon the measurements and projections by utilizing data from other systems, such as a wheel profiling system described in U.S. Pat. Nos. 5,636,026, 6,768,551, 8,140,250, or U.S. Patent Application Publication No. 2009/0055041.

Such external data can enable the computer system 40 to refine its models of the components (e.g., wheels) passing through the system and thus be more accurate, sensitive, and reliable. For example, an embodiment of the system can be located on a freight line (where there is no guarantee of seeing a given wheel regularly). The system can proceed to analyze each wheel in isolation based on a general wheel exemplar model, but even brand-new wheels can vary significantly as there are different diameter wheels and different manufacturers with somewhat different specific designs and processes involved. In this embodiment, the car identification sensors 44 can send the identity of the vehicle to the computer system 40, which can access (e.g., from the web or over a wired or wireless line) a database, such as UMLER, from a remote system 42. The UMLER database includes a large amount of data on specific cars and types of cars, including the wheel size and manufacturer. This would allow the computer system 40 to select from exemplar models or compiled resonance profiles, which are specific to the particular type of wheel passing through the system, rather than a more generic model, which would have elements of many larger and smaller wheels.

In another embodiment, this approach may be further refined. As described herein, an embodiment of the system may use input data from other systems, including the wheel measurement and profiling inventions of the inventors or of others. These measurements take into direct account the wear on the wheel to the moment it is passed through the system, and—using accumulated records of worn wheels, models derived from studies of such wheels, and/or the like—the computer system 40 can apply these measurements to create an expected resonance profile, which can be much more accurate for detecting departures from safe wear. Even simpler detectors for diameter, which are not so accurate as the installed profile systems can be utilized. Several simple diameter measurement approaches are possible, including those described in U.S. Pat. No. 8,006,559. In any event, data from any of these systems can be utilized by the computer system 40 in that they refine knowledge of the wheel derived from a database such as UMLER to account for at least a general level of wear.

Figure 7:
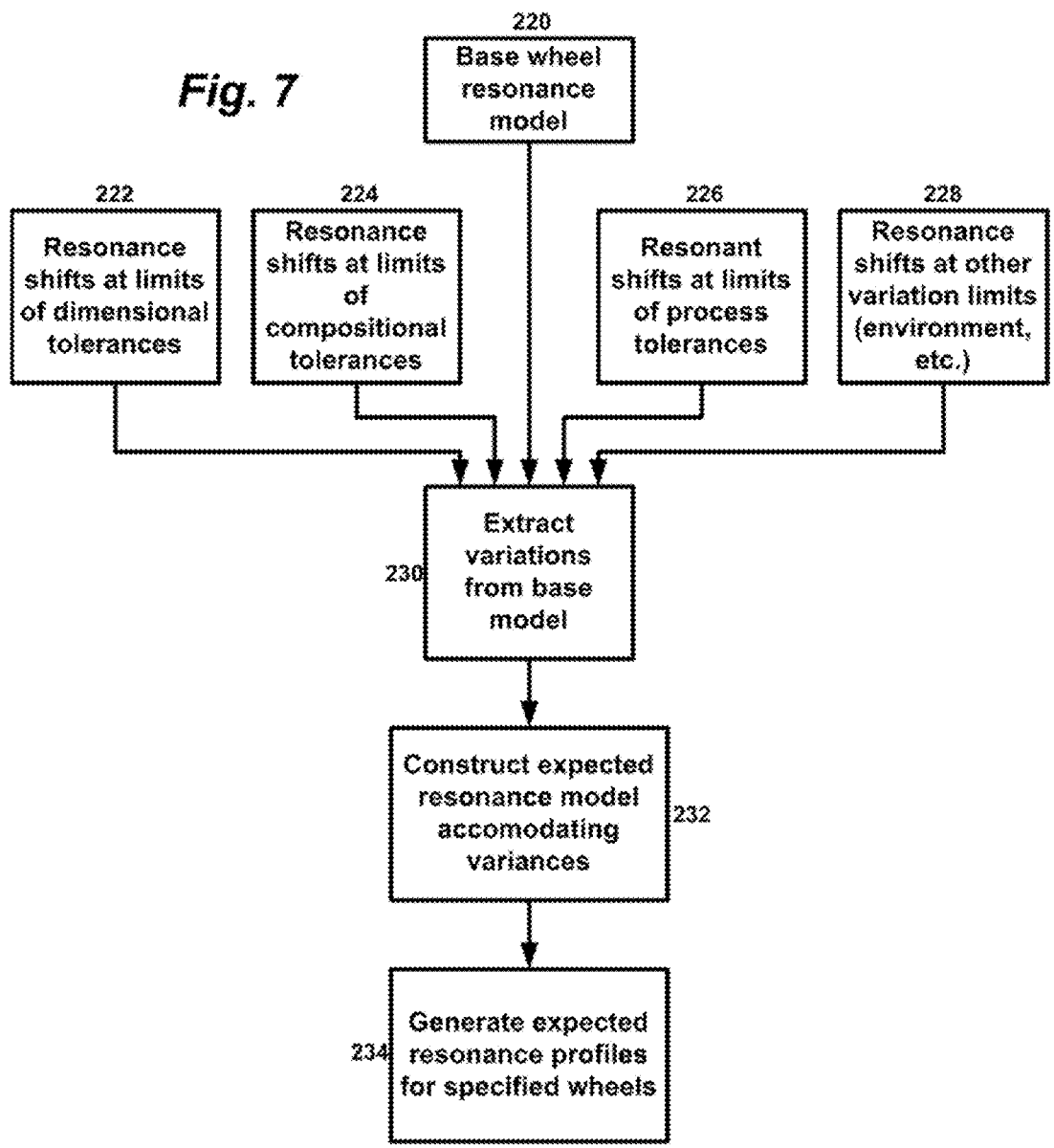
FIG. 7 is a flowchart illustrating one possible modeling process for creating exemplar resonance profiles.

In any event, to determine if the resonances seen in real wheels represent good or bad wheels, the computer system 40 can use models or templates with which to compare the wheel resonance signatures. One process for creating such a model is shown in FIG. 7. In this case, in action 220, the computer system 40 constructs a base wheel model based on some basic principles (for example, the linked-rings model discussed herein) or from some exemplar wheel physically modeled (in, for example, the form of a finite element model undergoing simulation) or via any other method (selecting one new manufactured wheel as the type exemplar, for example). A number of other inputs to the system are also shown: in action 222, the computer system 40 can obtain data corresponding to shifts in the resonance signature caused by variations in dimensions; by variations in wheel composition in action 224; by tolerated variations in processes in action 226; or by other factors which are not controllable (for instance, temperature variations) in action 228. The computer system 40 can determine these shifts by either theoretical means (changing the mathematical/simulated model's respective parameters between the permitted extremes) or by practical means (locating exemplar wheels which cover the maximum permitted variation in each category). In action 230, the computer system 40 can compare each additional input 222-228 with the base wheel resonance model to extract the variations in the various parameters of the resonance (amplitude, central frequencies, etc.). In action 232, the computer system 40 can incorporate these variations into the base model to create an expected resonance model which includes the full span of expected variation for the types of wheels modeled. From this model, the computer system 40 can generate a resonance profile/template with allowable error/variation matrices.

Note that this approach may be expanded—for example, the computer system 40 can incorporate variations of resonance from normal expected wear, or variations based on different manufacturers, etc.—and need not be "standalone" but may be incorporated as a part of a larger system. Another factor which can be evaluated by the computer system 40 is whether the resonances change depending on the load which a wheel carries. Railroad wheels are pre-stressed in a particular manner during manufacture, but it is well-known that acoustic signals are affected by varying stresses in target mediums. To this extent, an embodiment of the system calibrates the wheel data for the load on the car, as the greater loads will induce significantly greater stresses in the wheels. To allow this to be quantified for each passing car, a strain gauge or other method of measuring the weight on passing wheels can be installed in or under the rail—either the rail 12 preceding the system, under the isolated rail segment 14, as seen in FIG. 1a, and/or the like.

Figure 8:
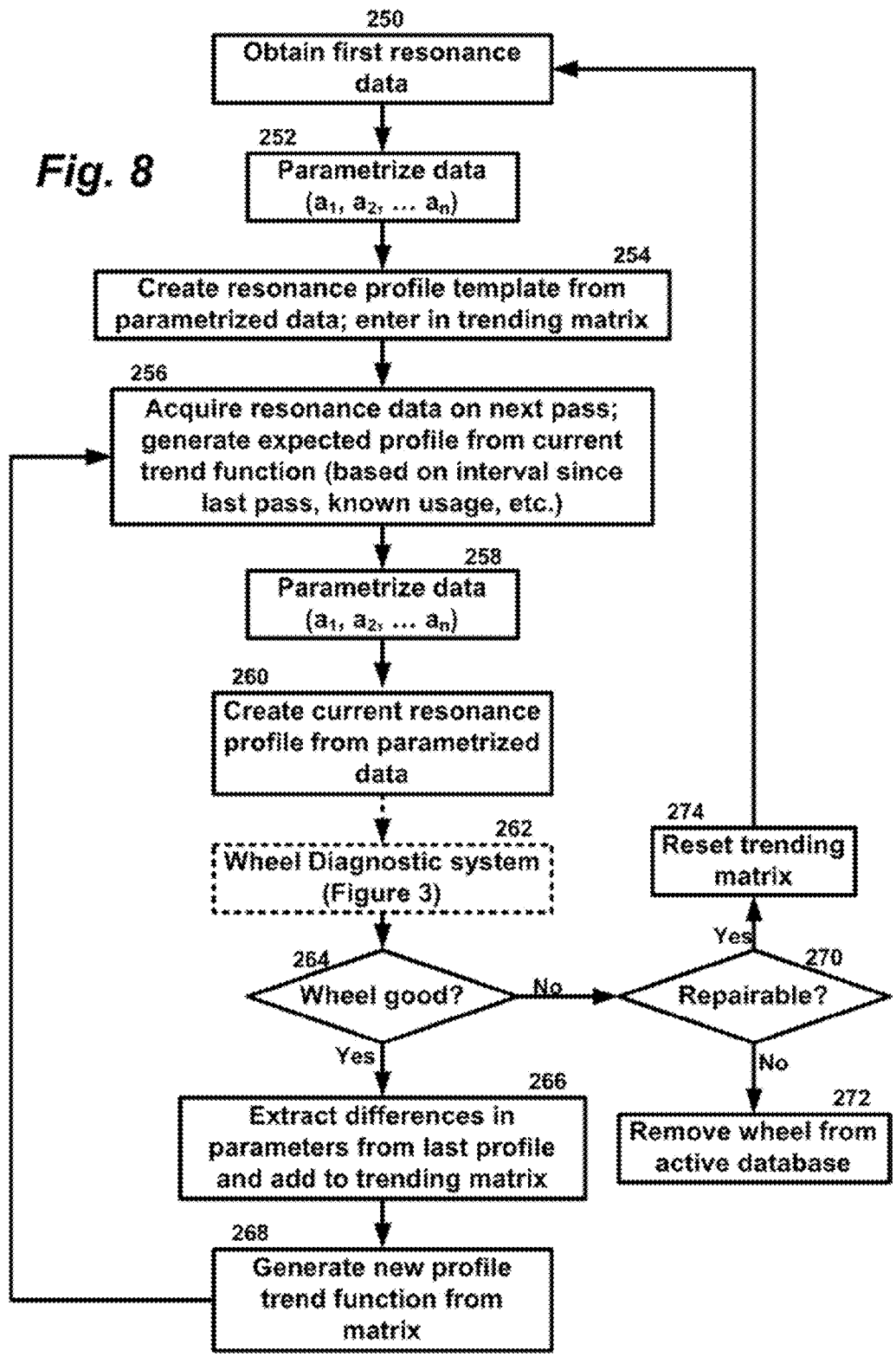
FIG. 8 is a flowchart illustrating one possible process for acquiring and trending resonance data according to an embodiment.

As discussed herein, an embodiment is installed in a transit or similar setting in which there is a "captive fleet" of cars whose wheels will consequently be seen by the system at some reasonably reliable intervals. For purposes of predictive maintenance and more accurate measurement, the computer system 40 can be configured to predict the changes expected in the wheel resonances, a process called trending. FIG. 8 shows one possible process to accomplish this. In action 250, on the initial passing of a wheel through the system, the computer system 40 can obtain the first resonance data. In action 252, the computer system 40 can parameterize this data and in action 254, the computer system 40 can create an initial resonance profile template with expected variance created from this parameterized data. The computer system 40 also can enter this data into a trending matrix, which can be expanded as additional data is accumulated for each given wheel as the trending matrix will contain the data from prior measurements, which can be used to calculate trends for the various resonance parameters.

In any event, during the next pass of the wheel through the system, in action 256, the computer system 40 can acquire current resonance data and use the current trend function on the last resonance profile template to adjust the template to the expected values for the current state. Note that the computer system 40 can take into account a number of factors in the trending function, including for example, time since last measurement, as—other factors being equal—a longer time since last measurement would indicate greater probability of wear and greater proportional resonance changes. Another factor can be a known use profile. For instance, if a particular track route was known to produce greater or lesser wear, including a proportion of time a car passed over that route, would affect the expected current resonance profile.

In action 258, the computer system 40 can parameterize the current resonance data and in action 260, the computer system 40 can create a current resonance profile. In action 262, the computer system 40 can send the current profile and the expected profile to a diagnostic system, which can return a value of good or bad for the wheel. In action 264, the computer system 40 can determine a next action based on the returned value. If the return value for the wheel is good, in action 266, the computer system 40 can compare the current wheel profile with the last wheel profile, extract the differences, and add these differences/changes to the trending matrix. In action 268, the computer system 40 can generate a new trending function using all the prior measurements of the wheel as recorded in the trending matrix, and the process can continue additional iterations from action 256. If the return value for the wheel is bad, in action 270, the computer system 40 can receive a decision, e.g., by a shop or by another automated system, as to whether the wheel can be returned to service (for example, by re-truing) or not. If the decision indicates that the wheel cannot be repaired (must be scrapped), in action 272, the computer system 40 can remove the wheel and associated data from the active database 272. The data may be retained for other uses (for example, developing larger-scale and more reliable models based on larger numbers of real wheels) but is no longer kept as an active wheel. If the decision indicates that the wheel can be repaired, the basic wheel identity/designation remains active, but the re-truing will in effect make the wheel a new physical entity.

Thus, in action 274, the computer system 40 can reset the trending matrix and the trending process returns to action 250. Many other possible processes, with more elaborate approaches and detail, may be envisioned by those skilled in the art.

Key to these operations is an ability for the computer system 40 (or another diagnostic system) to perform a comparison between the theoretical or expected resonance template/profile and the actual profile seen in the data. In theory, resonances are precise in their location, amplitude, and so on and will vary only with physical changes to the object. In the real world, however, there are numerous physical changes or conditions which may modify the resonances of a wheel in difficult-to-control ways. For example, a wheel may become coated with grease and dirt, which may muffle (reduce in amplitude) signals of all sorts; portions of the wheel may be encrusted with ice, become wet, or change in temperature, which may add resonances not seen previously, or more likely shift some other parameters of the resonances—compressing them or distorting them in various ways.

Figure 9:
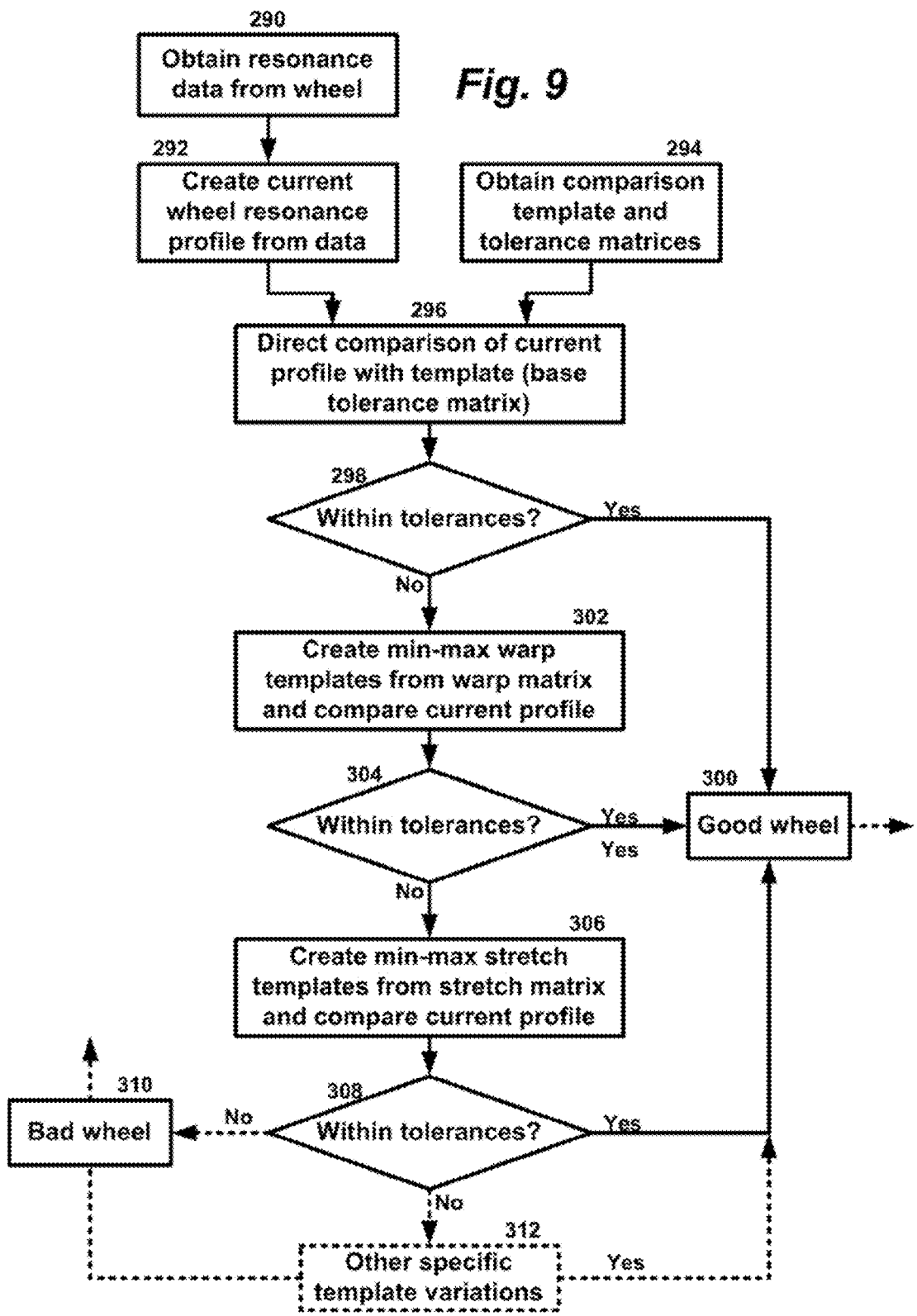
FIG. 9 is a flowchart illustrating a possible process for using multiple variations of template profiles to diagnose target objects according to an embodiment.

To automate the diagnostic process, the system can include a means to compensate for these challenges. FIG. 9 conceptually diagrams a method and process for providing the system with these capabilities according to an embodiment. In action 290, the computer system 40 can obtain an initial set of resonance data and in action 292, the computer system 40 can construct a current wheel resonance profile from this data. In action 294, the computer system 40 can access both a basic comparison template (such as one generated by a trending function from FIG. 8) and a number of other tolerance matrices, each of which can describe some function of variation in resonances derived from particular types of common physical differences or conditions. For example, the tolerance matrices can include a matrix which shows the degree of amplitude reduction seen with levels of dirt/grease coating from zero to the maximum seen, a matrix which describes the shift in resonant frequencies (stretching or compression) seen as a wheel is chilled or cooled, a matrix describing the distortion of waveform patterns (warp or skew) caused by ice coatings, and so on. Each of these different tolerance matrices can be applied to the basic comparison template to produce a template which represents a still-good wheel under these variant circumstances.

In any event, in action 296, the computer system 40 can compare the current profile with the basic template and in action 298, the computer system 40 can determine whether the resonance pattern falls within that template's tolerances. If it does, in action 300, the computer system 40 can designate the wheel as good. If it does not, in action 302, the computer system 40 can apply a next set of tolerance functions and matrix values (in this case, warp values) to the basic template and repeat the comparison. Again if in action 304, the computer system 40 determines that an acceptable match is produced, in action 300, the computer system 40 designates the wheel as good. However, if the match is still not acceptable, in action 306, the computer system 40 can apply a next tolerance function and matrix values and repeat the comparison. In action 308, the computer system 40 can determine if the wheel is within tolerances, and if so, in action 300, the computer system 40 can designate the wheel as good. If that is the last set of tolerance functions and matrix values and the computer system 40 determined that there was no match, in action 310, the computer system 40 can designate the wheel as bad. Alternatively, if more tolerance functions and matrix values exist, the computer system 40 also can examine each successively as indicated by action 312.

It is understood that an embodiment can create warp, skew, stretch, etc., functions as aggregate functions from all the possible conditions of interest rather than individual conditions. Similarly, an embodiment can create complex functions to describe the entire set of variations in a single aggregate. What approaches are used can depend on various other factors, including prevalence of specific conditions, computational complexity, and so on.

This description is not exhaustive and the embodiments of the invention described herein are understood to include any and all modifications, additions, derivations, and so on which would be evident to one skilled in the art.

To this extent, the invention described herein is not limited to the specific form of the description, but can be instantiated in many different forms. Following are some examples of other embodiments.

Many resonances lie in the "acoustic" region of the vibrational spectrum—from ~20 Hz up to 20 kHz—and others in the nearer ultrasonic regions of up to 50-100 kHz. In these regions, data may be acquired using a microphone of some sort. For example, an embodiment can use a parabolic microphone to gather the resonance data. In this embodiment, if appropriate diagnostic resonances exist within the broad acoustic region of the spectrum (including those areas above human hearing but within reasonable range of microphonic technology to receive), the resonances may be induced by piezoelectric, electromagnetic, or physical means and the resulting resonances recorded as sound (acoustic) signals by the parabolic microphone. A parabolic microphone offers multiple advantages over standard microphones. For example, it amplifies very strongly the sound at the focus of the microphone, while heavily attenuating noise external to the focus area. This permits the parabolic microphone to acquire longer usable sound samples which are less noisy than a standard microphone. The microphone also can be set much farther back from the rail, protecting this portion of the system from damage. The inventors have described these and other advantages of such approaches, as well as the location and focusing of such devices, in U.S. Pat. No. 8,326,582. This patent also describes related methods for analysis of acoustic signals which may be applied to this case as well and is therefore hereby incorporated by reference.

FIG. 10 illustrates an embodiment in which the rail itself may be a component of the sensor system. In this embodiment, there is no sensor head nor standard transducers indicated. Instead, within or above the isolating structure 20 in the fill 22 is set a more powerful vibration source/transducer 330 which through mechanical, electromagnetic, or other means causes the rail segment 14 itself to vibrate in such a manner as to induce the resonances into the wheel 10, which then in turn transfers these vibrations to the rail 14 to be detected by the source/transducer 330, or to any other receiver of vibratory or, if in the appropriate band, acoustic signals as described previously. This process is illustrated in FIG. 10. The vibrations 332 travel through the rail segment 14 inducing resonance vibrations 334 in the wheel 10 which in turn are transferred as vibration signals 336 into the rail segment 14. While this approach may require more power for the specific application, it may significantly simplify some portions of the design. For example, the embodiment does not require the transducers themselves to have direct contact with the wheel 10, which can be a very wearing process. In addition, sensor head 24 (FIG. 1*a*) requires on-track modifications which are highly vulnerable to dragging equipment and other common rail setting threats. As mentioned herein, the rail segment 14 need not be composed of the same materials as the adjacent rail 12. For this particular embodiment of the system, the rail segment 14 can be composed of other materials which would enhance the induction of a vibrational signal into the rail segment 14 and thus into the wheel 10, or which would permit the rail segment 14 itself to be the inducer of the signal (e.g., without the need for the transducer 330, as the rail segment 14 would itself be the transducer).

In an embodiment, integral mechanical signal induction can be utilized to induce the resonance signal. In general, the description herein, with the exception of the embodiment using the rail itself as the inducing component, has implied a piezoelectric, electromagnetic, or sometimes a side mounted "hammer" method of inducing a broad-band resonance signal into the target wheel. All of these methods require some method, such as the mounting 32 seen in FIGS. 1a-1c, to support the signal-inducing component and bring it into contact with the wheel 10. This is a potential point of failure for such a system. In addition, it is difficult to assure sufficient energy transfer in several situations to fully excite the wheel 10. In the rail-based induction embodiment, a significant challenge is to vibrate an entire section of track sufficiently to induce the desired resonances.

FIGS. 11a and 11b illustrate an embodiment which provides an integral method to induce resonances reliably, without the potential issues of either a separate and exposed support component or of having to somehow vibrate or otherwise trigger an impulse through the entirety of the rail section 14. FIG. 11a shows a side view of the isolated rail segment 14. In this case, rail segment 14 is a specially designed piece of rail with a vastly thickened "web" 360 to provide support around two excitation "pinger" assemblies 362. These assemblies 362 are embedded in and penetrate the fill 22 and isolating structure 20, and also include a hole 364 bored in the rail segment 14. The "ping" is delivered using a striker cylinder 366 which is accelerated in some manner to impact with force against a passing wheel's tread. The acceleration may be achieved by a mechanical piston at the base of the hole 364 or by other means. In FIGS. 11a and 11b, a coil gun mechanism composed of coils 368 is illustrated, which uses electromagnetic acceleration on a ferrous striker cylinder 366. An advantage of a coil gun or similar mechanism is that actuation of the pinger assembly 362 is performed without any wearable mechanical components except the striker cylinder 366 itself.

Moreover, the approach shown in FIGS. 11a and 11b resets itself through gravity alone. There is no need for mechanisms to return the unit to the rest condition. The acceleration, and thus magnitude of impact, may also be precisely controlled by the magnetic acceleration. This can address concerns of whether a sufficient excitation, and a reliably repeatable excitation, of the wheels can be achieved with some other mechanisms. In addition, the presence of the striker cylinder 366 will prevent debris from dropping far into the hole 364, and the hole may be cleared by a low-power "clean" actuation which causes the cylinder 366 to partially emerge from the hole 364. A pneumatic actuation mechanism can also be envisioned, in which the hole 364 is attached to a powerful source of compressed air which would perform the acceleration and/or cleaning functions. The striker cylinder may 366 be provided with a lower portion of substantially greater diameter than the top portion, and the hole 364 shaped such that the top of the cylinder 366 will never protrude beyond some distance, so that it is impossible to actually eject the cylinder 366 from the top of the hole 364.

Two separate assemblies 362 are shown in FIG. 11a as it is likely that wheels 10 going in a given direction will need to be "pinged" at different times. It is understood that some transducer mechanisms, such as the side mounted transducers 26 or in-rail transducer 28, or the parabolic microphone described herein, will be required to receive the signals, but the on-rail components can then be much lighter and lower in power as they need not provide the signal as well as receive the resonance data.

FIG. 11b shows an end-on view of this embodiment. In this figure, the installation 362 is shown as precisely centrally aligned within the rail. It is possible that in a real-life embodiment each of the two installations 362 might be slightly offset to properly impact with the wheels. In addition, the portion of the hole on the top of the rail can be machined in a way that reduces flow of the rail metal so as to keep the hole 364 as clear and undeformed as possible for the longest period of time.

In an embodiment, environmental signal-based resonance can be utilized to induce the resonance signal. In the process of traveling over a rail, a large amount of noise is generated which can amount to a broad-spectrum vibrational input. With appropriate noise processing and characterization, an embodiment may include a short section or sections of track equipped with microphones, input transducers, or other means of receiving vibration signals, with the concept and object being to detect and define the resonances generated by the natural noise currently present in the environment. Such an embodiment must carefully characterize the noise present as input to the wheel 10 as the input will affect a number of expected characteristics of the resonances, most notably the amplitude of induced resonances and to some extent, the specific resonances that would be expected to be most strongly present.

In an embodiment, the resonance can be utilized to perform rail quality characterization. In this case, the components such as the transducers 26 or 28 can be located on some sensor head 24 attached to a rail vehicle, which is equipped with data acquisition hardware and software, and in which the signals are induced into and read from the rail over which the rail vehicle is traveling. In this embodiment, some form of isolating damper on the relevant section of rail ahead and behind of the sensor head can be utilized. In any event, this design can evaluate resonances in the rail, rather than in a wheel, permitting the determination of whether the rail in question was still of acceptable quality. In the case of rail safety, a railroad is not, in the general case, interested in the specific question of what precise flaw exists within the rail. Rather, they are interested in whether the rail is safe for use. The technique of resonant ultrasound spectrographic analysis and related methods is ideal for this purpose.

The foregoing description of various embodiments of this invention has been presented for purposes of illustration and description. It is not intended to be exhaustive or to limit the invention to the precise form disclosed and inherently many more modifications and variations are possible. All such modifications and variations that may be apparent to persons skilled in the art that are exposed to the concepts described herein or in the actual work product, are intended to be included within the scope of this invention disclosure.

What is claimed is:

1. A method for resonant signal analysis-based inspection of a rail component, the method comprising:
  inducing a spectrum of frequencies into an in-situ rail component;
  detecting and recording resonances produced by the induced vibrations of a spectrum of frequencies in an in-situ rail component as resonance data;
  determining a set of characteristics of resonant peaks within each of a plurality of frequency bands of interest across a wide range of frequencies of the resonance data;

comparing the sets of characteristics with an expected resonance profile for the rail component, wherein the expected resonance profile includes a set of expected characteristics for each of the plurality of frequency bands of interest; and determining a condition of the rail component based on the comparing.

2. The method of claim 1, wherein the rail component is a railroad wheel.

3. The method of claim 2, further comprising selecting the spectrum of frequencies based on modeling of a set of characteristics of the railroad wheel.

4. The method of claim 2, further comprising selecting the spectrum of frequencies based on tests on a set of exemplar railroad wheels.

5. The method of claim 1, wherein the expected resonance profile is a sound-based parametric model using invariant feature sets representing a particular rail component or a particular type of rail component, and wherein the determining determines an overall condition of the rail component without regard to any particular defect.

6. The method of claim 1, wherein the expected resonance profile is based on a set of known rail components.

7. The method of claim 1, wherein the expected resonance profile is based on a set of prior inspections performed on the rail component.

8. The method of claim 7, further comprising refining the expected resonance profile prior to use based on a prediction based on the set of prior inspections.

9. The method of claim 1, further comprising refining the expected resonance profile based on an established database of vehicles relevant to the rail component.

10. A system for resonant signal analysis-based inspection of a rail component, the system comprising:

means for inducing vibrations of a spectrum of frequencies into an in-situ rail component;

means for detecting resonant vibrations created in the rail component by the induced vibrations; and a computer system for evaluating the rail component by performing a method including:

recording the detected resonant vibrations as resonance data for the rail component;

determining a set of characteristics of resonant peaks within each of a plurality of frequency bands of interest across a wide range of frequencies of the resonance data;

comparing the sets of characteristics with an expected resonance profile, wherein the expected resonance profile includes a set of expected characteristics for each of the plurality of frequency bands of interest; and determining a condition of the rail component based on the comparing.

11. The system of claim 10, wherein the rail component is a railroad wheel.

12. The system of claim 11, further comprising a segment of track having a length selected to only include a single railroad wheel for a rail vehicle at a time, and configured to be physically isolated from tracks on both sides of the segment.

13. The system of claim 10, wherein the means for inducing vibrations includes a piezoelectric device capable of inducing multiple selected frequencies.

14. The system of claim 10, wherein the means for inducing vibrations includes an electromagnetic device capable of inducing multiple selected frequencies.

15. The system of claim 10, wherein the means for inducing vibrations includes a rail over which the rail component is traveling.

16. The system of claim 10, wherein the means for inducing vibrations includes a striker moving through a substantially vertical hole in a rail over which the rail component is traveling.

17. The system of claim 10, wherein the means for detecting resonant vibrations includes the same device as the means of inducing resonant vibrations.

18. The system of claim 10, wherein the means for detecting resonant vibrations includes at least one of: a piezoelectric device or an electromagnetic device, configured to induce multiple selected frequencies.

19. The system of claim 10, wherein the means for detecting resonant vibrations includes a parabolic microphone.

20. A system for resonant signal analysis-based inspection of a railroad wheel, the system comprising:

means for inducing the resonant vibrations in the railroad wheel as the railroad wheel travels over a rail segment;

means for detecting resonant vibrations created in a railroad wheel during operation of the railroad wheel on a rail vehicle; and a computer system for evaluating the railroad wheel by performing a method including:

recording the detected resonant vibrations as resonance data for the railroad wheel;

determining a set of characteristics of resonant peaks within each of a plurality of frequency bands of interest across a wide range of frequencies of the resonance data;

comparing the sets of characteristics with an expected resonance profile for the railroad wheel, wherein the expected resonance profile includes a set of expected characteristics for each of the plurality of frequency bands of interest; and determining a condition of the railroad wheel based on the comparing.

21. The system of claim 20, wherein the means for inducing the resonant vibrations in the railroad wheel includes a set of transducers configured to maintain contact with the railroad wheel as it travels over at least a portion of the rail segment.

* * * * *